United States Patent [19]

Foglio et al.

[11] 4,018,776
[45] Apr. 19, 1977

[54] PROCESS FOR THE PREPARATION OF CEPHALOSPORINS FROM THE CORRESPONDING AZETIDINONE-THIAZOLINE DERIVATIVES

[75] Inventors: Maurizio Foglio; Paolo Masi; Antonino Suarato; Giovanni Franceschi, all of Milan, Italy

[73] Assignee: Societa' Farmaceutici Italia S.p.A., Milan, Italy

[22] Filed: Aug. 4, 1975

[21] Appl. No.: 601,586

[30] Foreign Application Priority Data

Aug. 7, 1974  United Kingdom ............ 34724/74

[52] U.S. Cl. ...................... 260/243 C; 204/158 R
[51] Int. Cl.² ...................... C07D 501/08
[58] Field of Search ............... 260/243 C

[56] References Cited
UNITED STATES PATENTS 3,705,892   12/1972   Cooper ............... 260/243 C X Primary Examiner—Nicholas S. Rizzo
Assistant Examiner—Diana G. Rivers
Attorney, Agent, or Firm—Stevens, Davis, Miller & Mosher

[57] ABSTRACT

A process is disclosed for preparing a cephalosporin of structure:

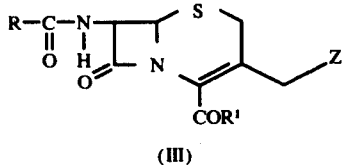

(III)

where R is selected from the class consisting of hydrogen, alkyl having from 1 to 4 carbon atoms, cyanomethyl, thienyl-methyl, furyl-methyl, naphthyl-methyl, phenyl-methyl, phenoxy-methyl, phenyl-isopropyl, phenoxy-isopropyl, pyridyl-4-thiomethyl, tetrazolyl-1-methyl;

$R^1$ is selected from the class consisting of hydroxy, alkoxy having from 1 to 4 carbon atoms, trichloroethoxy, benzyloxy, p-methoxy-benzyloxy, p-nitrobenzyloxy, benzhydryloxy, triphenylmethoxy, phenacyloxy, p-halophenacyloxy; and Z is selected from the class consisting of hydrogen, hydroxy, —O—Alkyl, —O—CO—Alkyl, —Br, —I, —NH₂, —O—COCH₃, —O—CO—NH₂, and an —S-mononuclear nitrogen heterocyclic ring,
wherein a compound of structure:

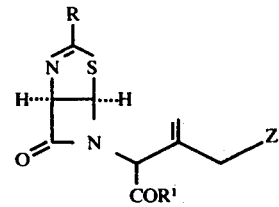

where R, $R^1$ and Z have the above meanings, is reacted with iodine in a suitable aqueous solvent at a temperature between 5° and 80° C in the presence of an oxide of a heavy metal or with a free radical initiator under the influence of light or heat, to give a compound of structure:

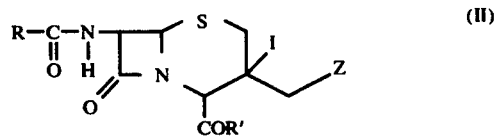

(II)

in which R, $R^1$ and Z have the above meanings,
and the said intermediate (II) is reacted in a suitable solvent with a compound selected from the class consisting of inorganic and organic bases to finally give the desired compound (III) which is then isolated and purified in per se known manner.

2 Claims, No Drawings

PROCESS FOR THE PREPARATION OF CEPHALOSPORINS FROM THE CORRESPONDING AZETIDINONE-THIAZOLINE DERIVATIVES

This invention refers to cephalosporins. More particularly, this invention relates to a new process for the preparation of cephalosporins of structure (III) starting from the corresponding azetidinone-thiazoline derivatives of structure (I) through intermediates of structure (II), according to the following reaction scheme:

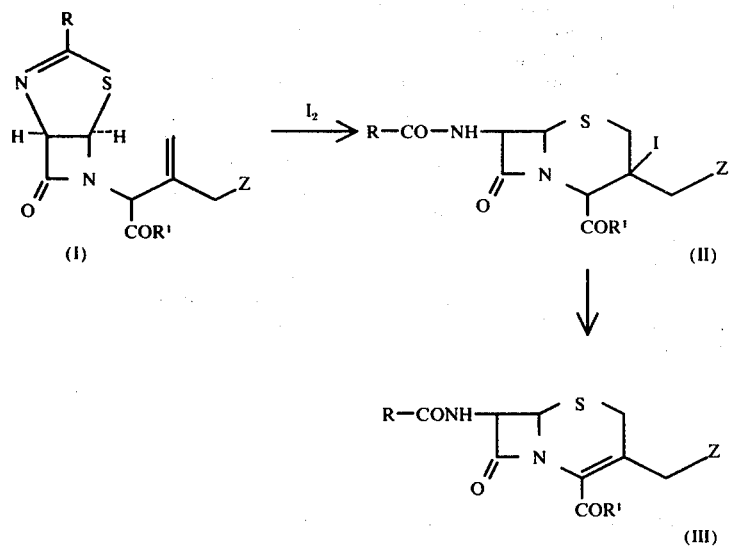

where R is selected from the class consisting of hydrogen, alkyl having from 1 to 4 carbon atoms, cyano-methyl, thienyl-methyl, furyl-methyl, naphthyl-methyl, phenyl-methyl, phenoxy-methyl, phenyl-isopropyl, phenoxy-isopropyl, pyridyl-4-thiomethyl, tetrazolyl-1-methyl;

$R^1$ is selected from the class consisting of hydroxy, alkoxy having from 1 to 4 carbon atoms, trichloroethoxy, benzyloxy, p-methoxybenzyloxy, p-nitrobenzyloxy, benzhydryloxy, triphenyl-methoxy, phenacyloxy, p-halo phenacyloxy; and Z is selected from the class consisting of hydrogen, hydroxy, O-Alkyl, O-CO-Alkyl, —Br, —I, —$N_3$, —$NH_2$, —$OCOCH_3$, —$OcONH_2$, and an —S— mononuclear nitrogen heterocyclic ring.

It has been found that compounds of structure (I) can be transformed directly into the corresponding 3-iodocepham of structure (II) by treatment with iodine under suitable conditions.

The reaction is carried out by reacting the starting material (I) dissolved in a suitable aqueous solvent at temperatures between 5° and 80° C with a small excess of iodine in the presence of an oxide of a heavy metal, such as mercuric and silver oxides, or with a free radical initiator such as azobisisobutyronitrile, benzoyl peroxide, t-butyl peroxide or similar compounds under the influence of light or heat.

Compounds of structure (II) may be isolated in good yields and may be easily transformed into the corresponding cephalosporins of formula (III) by mild treatment, in suitable solvents, with inorganic or organic bases such as KOH; $Na_2CO_3$; $NH_4OH$; aliphatic, aromatic and heterocyclic amines; quaternary alkylammonium bases; and basic resins.

The following non-limiting examples serve to illustrate the invention:

EXAMPLE 1

Methyl-7-phenoxyacetamido-3-iodo-3-methylcepham-4-carboxylate

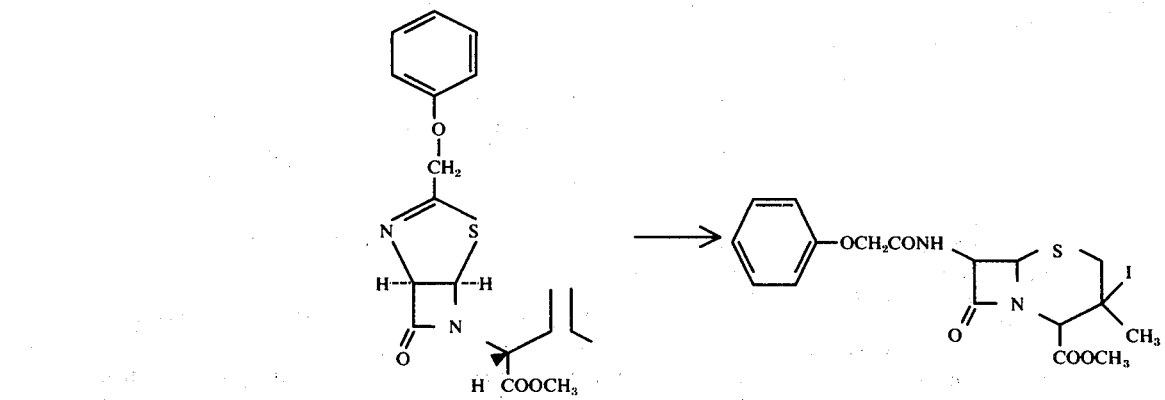

To a stirred solution of methyl-α-isopropenyl-3-phenoxymethyl-1α, 5α-4-thia-2,6-diaza-[3.2.0.]-2-heptene-6-acetate-7-one (356 mg) in tetrahydrofuran (50 ml), containing 0.5 ml of $H_2O$, iodine (200 mg), and yellow mercuric oxide (300 mg), are slowly and simultaneously added at room temperature. After 5 hours, the reaction mixture is filtered, evaporated to dryness, and the residue chromatographed to give methyl-7-phenoxyacetamido-3-iodo-3-methyl-cepham-4-carboxylate in good yields.

Rf = 0.33 (silica gel plates; the solvent system is benzene: petrol ether: ethylacetate, 70 : 10 : 40).

| IR(CHCl₃) | : 3404 | cm⁻¹ | (N-H) |
|---|---|---|---|
| | 1762 | " | (C=O β-lactam) |
| | 1734 | " | (C=O ester) |
| | 1688 | " | (C=O amide) |

NMR (CDCl₃) : 2.17δ(s, 3H,

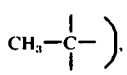), 2.73 and 3.08δ(two d, J$^{gem}$=15.0 Hz, 2H, C(2)H₂), 3.79δ(s, 3H,COOCH₃), 4.61δ(s, 2H, O—CH₂—CO), 4.87δ(s, 1H, C(4)H), 5.33δ(d, J=4.5 Hz, 1H, C(6)H), 5.68δ(dd, J=4.5 Hz and 10.0 Hz, 1H, C(7)H), 6.85-7.40δ(m, 5H, H arom.) and 7.61δ(d, J~10Hz, 1H, NH).

EXAMPLE 2

Methyl-7-phenoxyacetamido-3-iodo-3-methylcepham-4-carboxylate

A solution of methyl-α-isopropenyl-3-phenoxymethyl-1α,5α-4-thia-2,6-diaza-[3.2.0.]-2-heptene-6-acetate-7-one (356 mg) in tetrahydrofuran (50 ml), containing 0.5 ml of H₂O, iodine (200 mg), and azo-bis-isobutyronitrile (30 mg), is kept at 60° C for 1 hour. The solvent is next evaporated to dryness and the residue chromatographed to give methyl-7-phenoxyacetamido-2-iodo-3-methylcepham-4-carboxylate.

EXAMPLE 3

Methyl-7-phenoxyacetamido-3-methyl-3-cephem-4-carboxylate

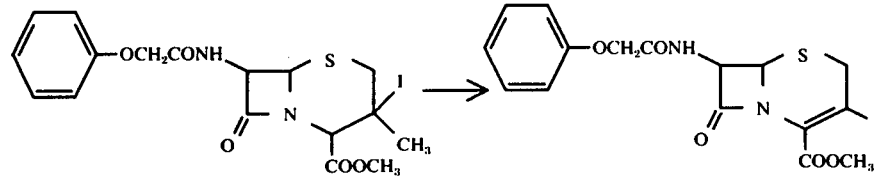

A solution of methyl-7-phenoxyacetamido-3-iodo-3-methylcepham-4-carboxylate (100 mg) in chloroform (10 ml) is treated with 1 equivalent of triethylamine and left overnight at room temperature. The reaction mixture is washed with acidified water, dried over anhydrous Na₂SO₄, and evaporated to dryness to give pure methyl-7-phenoxyacetamido-3-methyl-3-cephem-4-carboxylate identical to a standard sample.

What is claimed is:

1. A process for preparing a celphalosporin of structure:

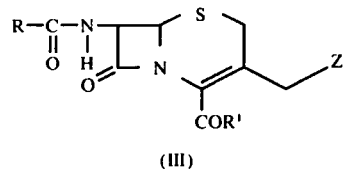

(III)

where R is selected from the class consisting of hydrogen, alkyl having from 1 to 4 carbon atoms, cyanomethyl, thienyl-methyl, furyl-methyl, naphthyl-methyl, phenyl-methyl, phenoxy-methyl, phenyl-isopropyl, phenoxy-isopropyl, pyridyl-4-thiomethyl, and tetrazolyl-1-methyl;

R' is selected from the class consisting of hydroxyl, alkoxy having from 1 to 4 carbon atoms, trichloroethoxy, benzyloxy, p-methoxy-benzyloxy, p-nitrobenzyloxy, benzhydryloxy, triphenylmethoxy, phenacyloxy, and p-halophenacyloxy;

and Z is selected from the class consisting of hydrogen, hydroxyl, —O—Alkyl, —O—CO-Alkyl, —Br, —I, —N₃, —O-COCH₃, —NH₂, —O—CO—NH₂, and 2-mercapto-5-methyl-1,3,4-thiadiazole;

wherein a compound (I) of structure:

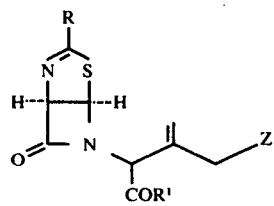

in which R, R¹ and Z have the above meanings, is reacted with iodine in an aqueous solvent at a temperature between 5° and 80° C in the presence of mercuric oxide or with azo-bis-isobutyronitrile under the influence of light or heat, to give an intermediate (II) of structure:

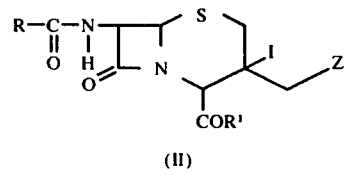

(II)

in which R, R¹ and Z have the above meanings, and the said intermediate (II) is then reacted in a chloroform solution with triethylamine or pyridine to give the desired compound (III) which is then isolated and purified.

2. A process as defined in claim 1, wherein the aqueous solvent is aqueous tetrahydrofuran.

* * * * *